(12) United States Patent
Scalice et al.

(10) Patent No.: US 11,921,107 B2
(45) Date of Patent: Mar. 5, 2024

(54) ASSAY DEVICE HAVING CONTROLLABLE SAMPLE SIZE

(71) Applicant: ORTHO-CLINICAL DIAGNOSTICS, INC., Raritan, NJ (US)

(72) Inventors: Edward R. Scalice, Penfield, NY (US); Philip C. Hosimer, Rochester, NY (US); Zhong Ding, Pittsford, NY (US); James D. Kanaley, Honeoye Falls, NY (US); David A. Tomasso, Rochester, NY (US); Daniel P. Salotto, Rochester, NY (US); Timothy C. Warren, Rochester, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 159 days.

(21) Appl. No.: 16/896,034

(22) Filed: Jun. 8, 2020

(65) Prior Publication Data
US 2020/0300841 A1 Sep. 24, 2020

Related U.S. Application Data

(62) Division of application No. 13/744,543, filed on Jan. 18, 2013, now Pat. No. 10,712,340.

(60) Provisional application No. 61/588,899, filed on Jan. 20, 2012.

(51) Int. Cl.
*G01N 33/53* (2006.01)
*G01N 33/543* (2006.01)

(52) U.S. Cl.
CPC ......... *G01N 33/5302* (2013.01); *G01N 33/53* (2013.01); *G01N 33/54388* (2021.08)

(58) Field of Classification Search
None
See application file for complete search history.

(56) References Cited

U.S. PATENT DOCUMENTS

| 5,120,643 | A | 6/1992 | Ching |
| 5,187,100 | A | 2/1993 | Matzinger |
| 5,559,041 | A | 9/1996 | Kang |
| 5,607,863 | A | 3/1997 | Chandler |
| 5,714,389 | A | 2/1998 | Charlton |
| 6,139,800 | A | 10/2000 | Chandler |

(Continued)

FOREIGN PATENT DOCUMENTS

| CN | 1764839 | 4/2006 |
| CN | 101203311 | 6/2008 |

(Continued)

*Primary Examiner* — Rebecca M Giere
(74) *Attorney, Agent, or Firm* — K&L Gates LLP; Louis C. Cullman; Dennis A. Majewski

(57) ABSTRACT

Disclosed is an assay device which comprises a liquid sample addition zone, a reagent zone, a detection zone, and a wicking zone, all defining a fluid flow path. The device further comprises a reagent addition zone along and in fluid communication with the fluid flow path downstream of the sample addition zone and upstream of the detection zone. An interrupting wash is added at this reagent addition zone in accordance with the method of the subject invention to control sample volume. The interrupting wash fluid is added at a predetermined fill volume on the chip device and also serves to wash the detection channel and fill the remaining chip volume.

17 Claims, 9 Drawing Sheets

(56) References Cited

U.S. PATENT DOCUMENTS

| | | |
|---|---|---|
| 6,228,660 B1 | 5/2001 | May |
| 6,372,542 B1 | 4/2002 | Martin |
| 6,733,682 B1 | 5/2004 | Björkman |
| 6,811,736 B1 | 11/2004 | Ohman |
| 6,884,370 B2 | 4/2005 | Ohman |
| 7,416,700 B2 | 8/2008 | Buechler |
| 7,972,872 B2 | 7/2011 | Shida |
| 8,999,730 B2 | 4/2015 | Oyamada |
| 9,689,870 B2 | 6/2017 | Ding |
| 10,082,502 B2 | 9/2018 | Kanaley |
| 2004/0023412 A1 | 2/2004 | Carlsson |
| 2006/0134802 A1 | 6/2006 | Donati |
| 2006/0285996 A1 | 12/2006 | Ohman |
| 2006/0289787 A1 | 12/2006 | Ohman |
| 2007/0231883 A1 | 10/2007 | Lindstrom |
| 2010/0035245 A1* | 2/2010 | Stiene ................ C12Q 1/6834 435/7.1 |
| 2010/0055716 A1 | 3/2010 | Tsutsui |
| 2010/0248394 A1* | 9/2010 | Ohman ............ B01L 3/502746 436/518 |
| 2011/0076697 A1* | 3/2011 | Ruvinsky ........... G01N 33/6887 435/7.25 |

FOREIGN PATENT DOCUMENTS

| | | | |
|---|---|---|---|
| CN | 102414561 | | 4/2012 |
| EP | 2618151 | | 7/2013 |
| JP | H07318560 | | 12/1995 |
| JP | H09506971 | | 7/1997 |
| JP | 2006524815 | | 11/2006 |
| JP | 2010054308 | | 3/2010 |
| JP | 2011117906 | | 6/2011 |
| JP | 4758341 | | 8/2011 |
| WO | 99/36780 | | 7/1999 |
| WO | WO 9936780 | * | 7/1999 |
| WO | 99/60402 | | 11/1999 |
| WO | 03/103835 | | 12/2003 |
| WO | 2004097419 | | 11/2004 |
| WO | 2005/089082 A2 | | 9/2005 |
| WO | 2005/118139 | | 12/2005 |
| WO | 2006/137785 | | 12/2006 |
| WO | 2007/149042 | | 12/2007 |
| WO | 2010/129302 | | 11/2010 |
| WO | 2013109821 | | 7/2013 |

* cited by examiner

ASSAY DEVICE HAVING CONTROLLABLE SAMPLE SIZE

CROSS REFERENCE TO RELATED APPLICATIONS

This patent application is a divisional of U.S. patent application Ser. No. 13/744,543, filed Jan. 18, 2013, now U.S. Pat. No. 10,712,340, which claims priority to U.S. Provisional Application No. 61/588,899, filed Jan. 20, 2012, the disclosures of which are incorporated by reference in their entirety.

FIELD OF THE INVENTION

The present invention relates to the field of diagnostic assays, and n particular to lateral flow assays where an analyte to be detected is present in a biological or non-biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet ail these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein, by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel, or tissue, comprising e.g. cellulose, wool, glass fiber, asbestos, synthetic fibers, polymers, or mixtures of the same.

Another type of assay device is a non-porous assay device having projections to induce capillary flow. Examples of such assay devices include the open lateral flow device as disclosed in PCT International Publication Nos. WO 2003/103835, WO 20051089082, WO 2005/118139, and WO 2006/137785, all of which are incorporated herein by reference in their entireties.

A known non-porous assay device is shown in FIG. 1. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay). Unbound dissolved conjugate material will be swept past the detection zone into the at least one wicking zone 5. Also shown in FIG. 1 are projections or micropillars 7.

An instrument such as that disclosed in US Patent Publication Nos. US20060289787A1 and US 20070231883A1, and U.S. Pat. Nos. 7,416,700 and 6,139,800, all of which are incorporated herein by reference in their entireties, is able to detect the bound conjugated material in the detection zone. Common labels include fluorescent dyes that can be detected by instruments which excite the fluorescent dyes and incorporate a detector capable of detecting the fluorescent dyes.

The sample size for such typical assay devices as shown in FIG. 1 are generally on the order of 200 µl. Such a sample size requires a venous blood draw from a medical professional such as a phlebotomist. There is an increasing need for lateral flow devices that are able to function with a much smaller sample size to accommodate the amount of blood available from a so-called "fingerstick" blood draw, which is on the order of 25 µl or less. Such a small amount of sample is the amount of blood in a drop of blood after pricking a finger tip with a lancet. Home blood glucose meters typically use a drop of blood obtained in such a fashion to provide glucose levels in blood. Such a smaller sample size would not require a medical professional to draw the blood and would provide greater comfort to the patients providing the sample for analysis.

To reduce sample size required, the dimensions of the lateral flow assay devices are reduced to accommodate the smaller sample size. However, it has been found that reducing the sample size and dimensions of the device provides inadequate conjugate in the detection zone and accordingly less signal that can be read by the instrument (in some instances up to a 5× lower signal) and poor sensitivity. The inadequate conjugate in the detection zone is believed to be due to reduced sample size and inefficient use of the sample in the device, amongst other conditions. Another drawback of reducing dimensions is that the width of the detection zone will also be reduced, again making less signal available that can be read by the instrument. Also, it has been found that a smaller device has reduced flow time and conjugate material contact time, resulting in less binding between the analyte in the sample and the conjugate material.

A need continues to exist for smaller sample volume assay devices that can accommodate smaller and smaller sample sizes, can accommodate various samples (such as whole blood), and can provide results with the required sensitivity and specificity.

SUMMARY OF THE INVENTION

The present invention is directed to such an assay device. An advantage of the smaller sample device according to the subject invention is the ability to control sample volume using an "interrupting wash". In its broadest concept, the interrupting wash can be any fluid. Fluids include reagent fluids (fluids containing a reagent) with a preferred interrupting fluid being a wash fluid. An interrupting wash fluid is added at a predetermined fill volume on the chip device which controls sample volume and also serves to wash the detection channel and fill the remaining chip volume.

Accordingly, one aspect of the invention is directed to an assay device which comprises: a liquid sample addition zone; a reagent zone downstream and in fluid communication with the sample addition zone containing a reagent material; a detection zone in fluid communication with the reagent zone having capture elements bound thereto; and a wicking zone in fluid communication with the detection zone having a capacity to receive liquid sample flowing from the detection zone. In the device, the sample addition zone, the reagent zone, the detection zone and the wicking zone define a fluid flow path. The device further comprises a reagent addition zone along and in fluid communication with the fluid flow path downstream of the sample addition zone and upstream of the detection zone. The "interrupting wash" is added at this reagent addition zone (a fluid addition zone in its broadest concept) in accordance with the method of the subject invention.

Another aspect of the invention is thus directed to a method of controlling sample size in an assay device. The method comprises: providing a liquid sample addition zone; providing a reagent zone downstream and in fluid communication with the sample addition zone containing a reagent material; providing a detection zone in fluid communication with the reagent zone; and providing a wicking zone in fluid communication with the detection zone having a capacity to receive liquid sample flowing from the detection zone. The sample addition zone, the reagent zone, the detection zone and the wicking zone define a fluid flow path. The method includes further providing a reagent addition zone along and in fluid communication with the fluid flow path downstream of the sample addition zone and upstream of the detection zone. The method further comprises adding sample to the sample addition zone, wherein the sample moves through the fluid flow path; and adding a reagent to the reagent addition zone, wherein the reagent interrupts flow of the sample through the fluid flow path thereby controlling sample size within the fluid flow path. Preferably the reagent added is a wash fluid.

Yet another aspect of the invention is directed to a method of performing an assay on a liquid sample for the detection of one or more analytes of interest. The method comprises: providing a liquid sample addition zone; providing a reagent zone downstream and in fluid communication with the sample addition zone containing a reagent material; providing a detection zone in fluid communication with the reagent zone; providing a wicking zone in fluid communication with the detection zone having a capacity to receive liquid sample flowing from the detection zone, wherein the sample addition zone, the reagent zone, the detection zone and the wicking zone define a fluid flow path; and further providing a reagent addition zone along and in fluid communication with the fluid flow path downstream of the sample addition zone and upstream of the detection zone. The method further comprises adding a liquid sample containing the analyte of interest onto the sample addition zone; moving the sample by capillary action into the reagent zone wherein the sample dissolves the reagent material; flowing the sample away from the reagent zone with the dissolved reagent material therein into the detection zone by capillary action, wherein the analyte of interest is detected in the detection zone by reading a signal that is generated; and flowing the sample and any unbound material into the wicking zone. The method further comprises adding a reagent to the reagent addition zone, wherein the reagent interrupts flow of the sample through the fluid flow path thereby controlling sample size within the fluid flow path. Preferably the reagent added is a wash fluid.

Further objects, features and advantages of the present invention will be apparent to those skilled in the art from detailed consideration of the preferred embodiments that follow.

DETAILED DESCRIPTION OF PREFERRED EMBODIMENTS

Figure 1:
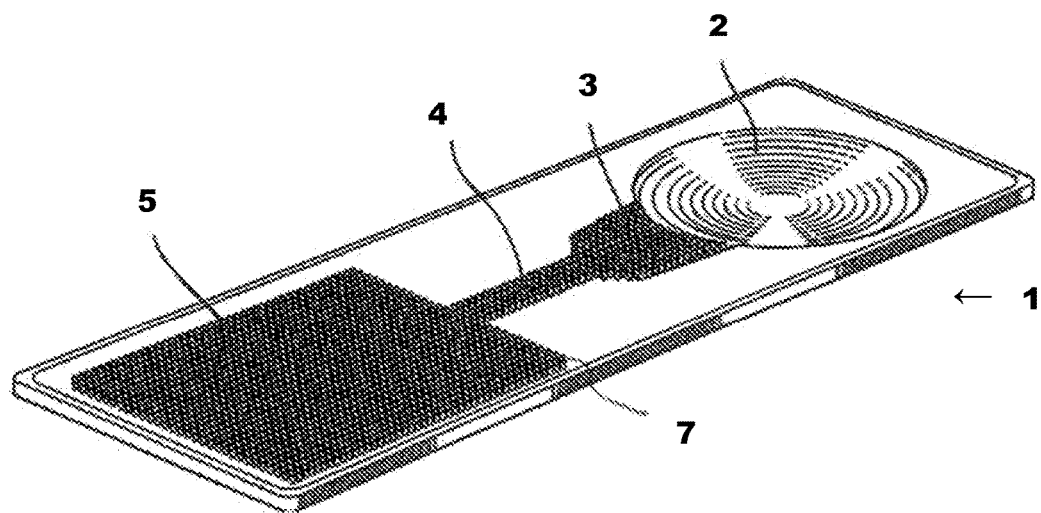
FIG. 1 shows a known assay device.

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and, acceptable to a person skilled in the art. The interval is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention are human or animal bodily fluids such as blood, plasma, serum, lymph, urine saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples but preferably to samples of whole blood, urine or sputum.

In other instances, the sample can be related to food testing, environmental testing, bio-threat or bio-hazard testing, etc. This is only a small example of samples that can be used in the present invention.

In the present invention, the determination based on lateral flow of a sample and the interaction of components present in the sample with reagents present in the device or added to the device during the procedure and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesitas, etc); markers of other specific diseases, e.g. acute diseases, such as coronary infarct markers (e.g. troponin-T, NT-proBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The terms "zone", "area" and "site" used in the context of this description, examples and claims to define parts of the fluid flow path on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

Figure 2:
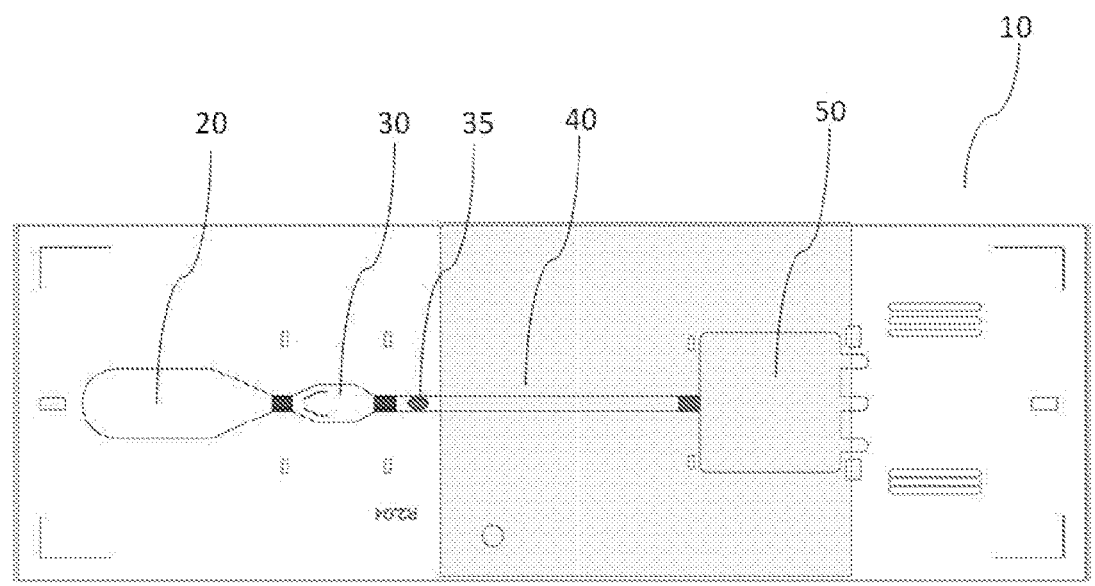
FIG. 2 shows a schematic view of an assay device according to one embodiment of the present invention.
Figure 3:
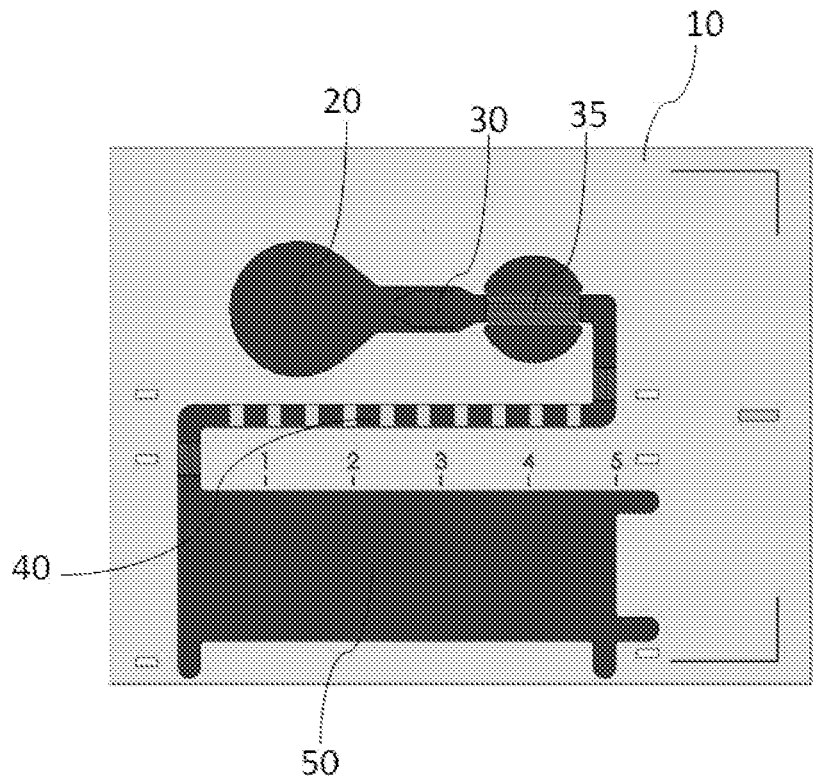
FIG. 3 shows a schematic view of an assay device according to another embodiment of the present invention.

The present invention is directed to a lateral flow assay device for determining the presence or amount of at least one analyte. FIGS. 2 and 3 show schematic views of preferred embodiments of such devices according to the invention. The assay device 10, has at least one sample addition zone 20, at least one reagent zone 30, at least one detection zone 40, and at least one wicking zone 50. The zones form a flow path by which sample flows from the sample addition zone to the wicking zone. The assay device also includes at least one reagent addition zone 35, preferably located between the reagent zone and the detection zone.

Components of the assay device (i.e., a physical structure of the device whether or not a discrete piece from other parts of the device) can be prepared from copolymers, blends, laminates, metallized foils, metallized films or metals. Alternatively, device components can be prepared from copolymers, blends, laminates, metallized foils, metallized films or metals deposited on one of the following materials: polyolefins, polyesters, styrene containing polymers, polycarbonate, acrylic polymers, chlorine containing polymers, acetal homopolymers and copolymers, cellulosics and their esters cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 1 shows projections 7.

In one embodiment the flow path is at least partially open. In another embodiment the flow path is entirely open. Open means that there is no lid or cover at a capillary distance. Thus the lid, if present as a physical protection for the flow path, does not contribute to the capillary flow in the flow path. An open lateral flow path is described for example in the following PCT International Publication Nos. WO 2003/103835, WO 2005/089082; WO 2005/118139; WO 2006/137785; and WO 2007/149042, all of which are incorporated herein by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US Patent Publication No. 2006/0285996, which is incorporated herein by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably about 40 to about 100 µm, and a gap or gaps between the projections of about 3 to about 200 µm, preferably about 5 to about 50 µm or about 10 to about 50 µm from each other. The flow channel may have a length of about 5 to about 500 mm, preferably about 10 to about 100 mm, and a width of about 0.3 to about 10 mm, preferably about 0.3 to about 3 mm, preferably about 0.5 to about 1.5 mm, and preferably about 0.5 to about 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone, also referred to as the liquid sample addition zone, receives sample from a sample dispenser, such as a pipette. The sample is typically deposited onto the top of the zone. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 1. In those devices that can use finger stick volumes of blood, the sample can be directly touched off from the finger, or by a capillary pipette such as described in copending application entitled "Controlling Fluid Flow Through An Assay Device" (U.S. Provisional Appl. No. 61/588,772, filed Jan. 20, 2012, first named inventor: James Kanaley), incorporated herein by reference in its entirety.

A filter material (FIG. 4) can be placed in the sample addition zone to filter particulates from the sample or to filter red blood cells from blood so that plasma can travel further through the device.

Located between the sample addition zone and the detection zone is a reagent zone. The reagent zone can include reagent(s) integrated into the analytical element and are generally reagents, useful in the reaction (binding partners such as antibodies or antigens for immunoassays, substrates for enzyme assays, probes for molecular diagnostic assays) or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. The amount of reagent in the reagent zone can be adjusted by the length of reagent deposited into the device while maintaining the same reagent width. The amount of reagent can also be adjusted by changing the width while maintaining the length. The amount of reagent can further be adjusted by changing both width and length simultaneously. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are, for instance, but are not limited to, luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}$I and $^{32}$P.

Suitable enzymatic labels are, for instance, but are not limited to, horseradish peroxidase, beta-galactosidase, luciferase, alkaline phosphatase and the like.

Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in a "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Located in the fluid flow path, before or after the reagent zone and before the detection zone, is a reagent addition zone. The reagent addition zone 35 is shown in FIG. 3. In its broadest concept, the reagent addition zone is a fluid addition zone. Such a fluid could be a reagent fluid, and preferably is a wash fluid. The reagent addition zone can allow addition of a reagent externally from the device. More particularly, the reagent addition zone is used to add an interrupting reagent that may be used to wash the sample and other unbound components present in the fluid flow path into the wicking zone. In a preferred embodiment the reagent addition zone 35 is located after the reagent zone 30 (see FIG. 3).

The reagent plume from the reagent zone should be as wide as possible to cover as much of the width of the detection zone as possible. One method for increasing the width of the reagent plume is described in copending application entitled "Assay Device Having Multiple Reagent Cells" (U.S. Provisional Appl. No. 61/588,738, filed Jan. 20, 2012, first named inventor: Zhong Ding) which is incorporated herein by reference in its entirety. In summary, multiple areas having reagent material (hereinafter referred to as "reagent cells") in a reagent zone along with elements to recombine multiple flow streams that result from the multiple reagent cells into one flow stream results in a more desirably mixed, wider agent plume as it leaves the reagent zone and enters the detection zone.

Downstream from the liquid sample zone and the reagent zone is the detection zone which is in fluid communication with the sample addition zone. The detection zone may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Lower Volume Assay Device Having Increased Sensitivity" (U.S. Provisional Appl. No. 61/588,758, filed Jan. 20, 2012, first named inventor: Phil Hosimer) incorporated herein by reference in its entirety, are significantly narrower, e.g. 1.5 mm or less.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality.

The detection zone can include multiple detection zones. The multiple detection zones can be used for assays that include one or more markers. In the event of multiple detection zones, the capture elements can include multiple capture elements, such as first and second capture elements.

The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the reagent zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the reaction zone or those added through the reagent addition zone. The reagent plume can include the conjugate having both the detection element and binding partner, in which case it is often referred to as a conjugate plume.

Downstream from the detection zone is a wicking zone in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in US Patent Publication Nos. US 2005/0042766 and US 2006/0239859, both of which are incorporated herein by reference in their entireties. Wicking zones are also described in copending patent application entitled "Controlling Fluid Flow Through An Assay Device" (U.S. Provisional Appl. No. 61/588,772, filed Jan. 20, 2012, first named inventor: James Kanaley), incorporated herein by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay performed on the assay device of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US Patent Publication No. 2007/0231883 and U.S. Pat. No. 7,416,700, both of which are incorporated herein by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention is directed to a method of performing an assay on a liquid sample for the detection of one or more analytes of interest. A liquid sample containing the analyte(s) of interest is deposited onto the sample addition zone of the device, such as through a port in the housing of the device, or by touching off a finger directly onto the sample addition zone in the case of a fingerstick blood draw. The sample moves by capillary action through an optional filter, and into the reagent zone where it dissolves the reagent material. In a preferred embodiment, the sample is reacted with a detection element in the case of a sandwich-type assay, either directly or indirectly, such as through an antibody. The sample flows away from the reagent zone having a dissolved reagent plume as it flows into the detection zone.

Next the sample moves by capillary action into the detection zone. In the detection zone, a signal representative of an analyte or control is produced. In a preferred embodiment the sample or one or more reagents having a detection element is captured in the detection zone, such as by antibodies on the surface of the detection zone and a signal representative of the presence or concentration of the analyte(s) or control(s) is produced. The reader or detection instrument as described above is then used to read the signal that is produced in the detection zone to determine the presence or concentration of the analyte(s) or control(s). The sample moves from the detection zone and into, the wicking zone. The reader may read the signal immediately or a short time after the sample has moved through the detection zone. Also, one or more washes may follow the sample through the device to wash any unbound reagents, such as detection elements, away from the detection zone.

The method, assay device, and reader according to an embodiment of the invention have many advantages. The "interrupting wash" concept can be utilized with various assay devices such as described in copending applications entitled "Low Volume Assay Device Having Increased Sensitivity" (U.S. Provisional Appl. No. 61/588,758, first named inventor: Phil Hosimer), "Assay Device Having Multiple Reagent Cells" (U.S. Provisional Appl. No. 61/588,738, first named inventor: Zhong Ding), "Assay Device Having Uniform Flow Around Corners" (U.S. Provisional Appl. No. 61/588,745, first named inventor: James Kanaley), "Controlling Fluid Flow Through An Assay Device" (U.S. Provisional Appl. No. 61/588,772, first named inventor James Kaneley), and "Assay Device Having Multiplexing" (U.S. Provisional Appl. No. 61/588,779, first named inventor: Sue Danielson), all filed Jan. 20, 2012 and all incorporated herein by reference in their entireties.

Figure 4:
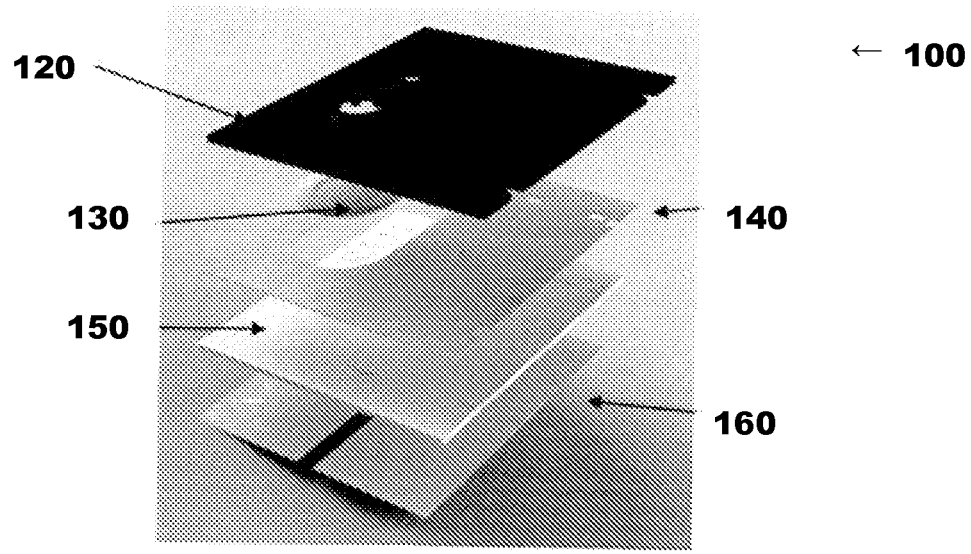
FIG. 4 shows an exploded view of the layered construction of an assay device package according to the present invention.

The assay device according to the subject invention can be packaged as shown in FIG. 4. The packaging 100 includes all of the functional elements necessary for assay performance, such as: top cover 120, filter 130, hydrophilic tape 140, assay device (chip) 150, and base cover 160.

It is to be understood that this invention is not limited to the particular embodiments shown herein. The following examples are provided for illustrative purposes and are not intended to limit the scope of the invention since the scope of the present invention is limited only by the appended claims and equivalents thereof.

EXAMPLES

Example 1

Plastic substrate chips made of Zeonor (Zoon, Japan) having oxidized dextran on the surface for covalent immobilization of proteins via Schiff base coupling were used. For NTproBNP chips, fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Sample was added to the sample zone of the device and the capillary action of the micropillar array distributed the sample through the flow channel into the wicking zone. A typical assay time was about 10 minutes. The signal intensities from the fluorescently labeled complexes in the detection zone were recorded in a prototype line-illuminating fluorescence scanner. For carbamazepine chips, the carbamazepine detection reagent was prepared by covalently linking a carbamazepine hapten and a fluorescent label to bovine serum albumin (BSA). The phenobarbital detection reagent was prepared by covalently linking a phenobarbital hapten and a fluorescent label to BSA. Monoclonal carbamazepine and phenobarbital antibodies were deposited and dried to create the detection zones. Varying levels of NTproBNP, carbamazepine, and phenobarbital were spiked into human serum to generate data. Experiments used reduced volume chip designs (such as shown in FIG. 2) and reduced volume reduced footprint chip designs (such as shown in FIG. 3).

In the first embodiment of the invention whole blood from fingerstick samples is applied directly to a filter on the test device to separate the red blood cells from plasma. The plasma flows from the filter to the capillary spaces within the micropillar sample zone and proceeds by capillary flow to the end of the fluid flow path. Contact of the filter membrane to the micropillar surface of the sample zone is important for plasma to flow from the membrane. Where contact is made the capillary forces within the micropillar structure wick the plasma from the membrane to create a plasma flow.

In prior art chip designs, 200 uL whole blood is applied to the filter although only about 35 uL plasma is required for an assay. The efficiency of total sample usage is only 17.5%.

The present invention is intended for use with only 25 uL of whole blood on reduced volume chip designs and reduced volume reduced footprint chip designs. In order to obtain the required 9 uL plasma for the assay, the filtration efficiency must be at least 36% for a 25 uL whole blood sample with 45% hematocrit.

In another embodiment of the device whole blood can be applied directly to the micropillar surface without using a filter membrane to separate the plasma from the red blood cells. Since the viscosity of whole blood is much greater than serum or plasma the flow resistance within the micropillar space is also much greater which results in very slow flow or flow stoppages. Also, the viscosity of whole blood can vary widely due to large hematocrit differences among patients. In order to achieve consistent flow of whole blood within the micropillar space, methods to reduce flow resistance or increase capillary force were required.

In this embodiment flow of whole blood within the micropillar spaces was facilitated by addition of a small volume (1 µL or less) of a solution containing a non-hemolytic, non-ionic, good wetting surfactant in or near the sample addition zone of the reduced volume chip designs and reduced volume reduced footprint chip designs. Immediately following addition of this prewet solution, 10-15 µL of whole blood is added directly to the sample addition zone. The surfactant containing solution acts to reduce the surface tension and prevents accumulation of red bloods at the fluid front. Capillary forces within the micropillar structure advance flow of the whole blood through the reagent (conjugate) zone, down the detection (reaction) channel and into the wicking zone.

Addition of a hydrophilic tape over the detection (reaction) channel increases the capillary forces within the micropillar space and serves to further improve the flow of whole blood through the chip. The reaction of detection conjugate and capture immunomaterials with the target analyte takes place in the presence of whole blood. However, since red blood cells interfere with the optical measurement of detection conjugates they must be removed prior to the read being taken. This is accomplished by addition of wash step prior to the final reading.

The method according to the subject invention uses an interrupting wash to control sample volume as well as to remove red blood cells and other interfering substances from the detection zone (channel). Sample volume is controlled by adding the wash fluid at the point when the blood sample has filled the wick zone to a predetermined level. Since the micropillar structures are designed to fill row by row and in a uniform manner the flow can be monitored manually or by the instrument to determine when the sample has filled the chip to the targeted volume. When the targeted sample volume is achieved a wash fluid is added to the micropillar channel at a position upstream of the detection channel as shown in FIG. 2 for a reduced volume chip design or FIG. 3 for a reduced volume reduced footprint chip design in accordance with the subject invention.

A wash fluid droplet of 10 to 15 μL is applied to create a dome shaped droplet which flows in both directions to efficiently remove sample from the downstream detection (reaction) channel and prevents sample in upstream pillar space from entering the detection (reaction) channel.

Figure 5:
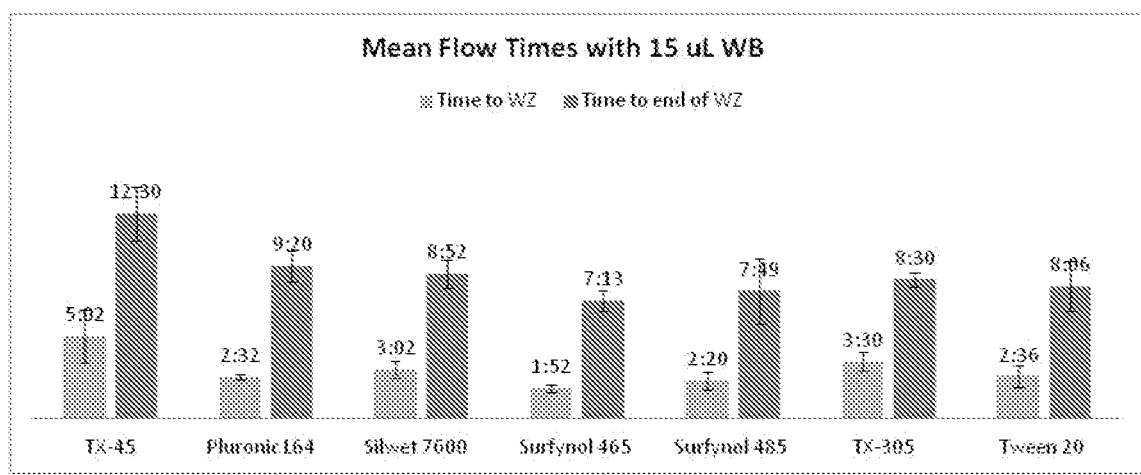
FIG. 5 shows mean flow times for whole blood on an assay device according to one embodiment of the present invention, with various surfactants deposited in the sample addition zone.

The wash fluid is typically composed of 0.1M sodium phosphate, 1% bovine serum albumin and 0.1% surfactant. Surfactants are necessary throughout the micropillar spaces to reduce surface tension to allow flow of fluid by capillary force. For prior art chip designs, Triton X-45 has been the preferred surfactant which is deposited and dried in the sample zone of the micropillar chip. To get whole blood to flow consistently in the chip deposition of TX-45 in the sample zone is not optimal. Several other non-ionic surfactants were shown to improve the flow rate of whole blood in the micropillar chips. FIG. 5 shows the mean flow times for whole blood to reach the start of the wick zone and time to reach the end of the wick zone in reduced volume chip designs with various surfactants deposited in the sample addition zone. Results show that whole blood flows faster with all the surfactants tested as compared with TX-45.

These results were obtained with a single whole blood sample. Since whole blood can vary greatly from person to person large variation in flow rates are expected. Slower flow rates were observed with increasing hematocrit level of samples and flow stoppages, were observed in samples with elevated hematocrit. Continuous flow of whole blood was obtained by use of the preferred surfactant in the sample addition zone and by addition of the pre-wet solution containing the same surfactant prior to sample addition.

The preferred prewet and wash solution contains the surfactant Surfynol® 485 or Surfynol® 465. Other preferred surfactants include Silwet® L7600, Tween® 20, Pluronic® L64, Surfactant 10G, Triton® X-305, Triton® X-45, and Triton® X-100. Surfactant levels of 0.05% to 1% are preferred.

Whole blood with interrupting wash test results: EDTA whole blood was obtained by venous collection and spiked with carbamazepine and phenobarbital to the levels indicated in Table 1. Reduced volume chip design with tape covering the wicking zone and approximately ⅔ of the detection zone (see FIG. 2), were used to evaluate the interrupting wash protocol. Each multiplex chip contained detection (reaction) zones consisting of an immobilized capture antibody for carbamazepine and a second detection (reaction) zone immobilized with a phenobarbital capture antibody. Conjugates of BSA and fluorophors of each drug were deposited in the reagent (conjugate) zone.

One microliter of wash fluid containing 1% BSA, 0.1% TX-100, in phosphate buffered saline was spotted in the sample zone and allowed to fully enter the micropillar space, then immediately followed by dispense of fifteen microliters of the whole blood sample. The fluid front was monitored by visual inspection until the fluid filled 50% of the wicking zone. Fifteen microliters of the same wash fluid was then applied directly over the channel (at the reagent addition zone) and the fluid front monitored until the wick zone was completely filled. The chip was assembled into the cartridge and read in the fluorescent reader.

TABLE 1

Whole Blood CRBM/PHBR Spiked Samples.

| ID | Fluid | Spike target (ug/mL)(CRBM/PHBR) | Vitros MicroSlide Mean Result ug/mL N = 2 | | Hematocrit |
|---|---|---|---|---|---|
| | | | CRBM | PHBR | |
| LV1 | no spike | na | 0 | 0 | 35% |
| LV2 | No CRBM/High PHBR | na/60-80 | 0 | 66.24 | 36% |
| LV3 | Mid CRBM/Mid PHBR | 4/12 | 4.3 | 10.89 | 36% |
| LV4 | High CRBM/No PHBR | 16-20/na | 21.8 | <3 | 36% |

An aliquot of each whole blood sample was centrifuged to separate plasma from whole blood. Plasma from each aliquot was collected and evaluated with the same chip design. Fifteen microliters of plasma was added directly to the sample zone. The chip was monitored by visual inspection and read in the fluorescent reader immediately after the wicking zone was determined to be completely filled.

Figure 6:
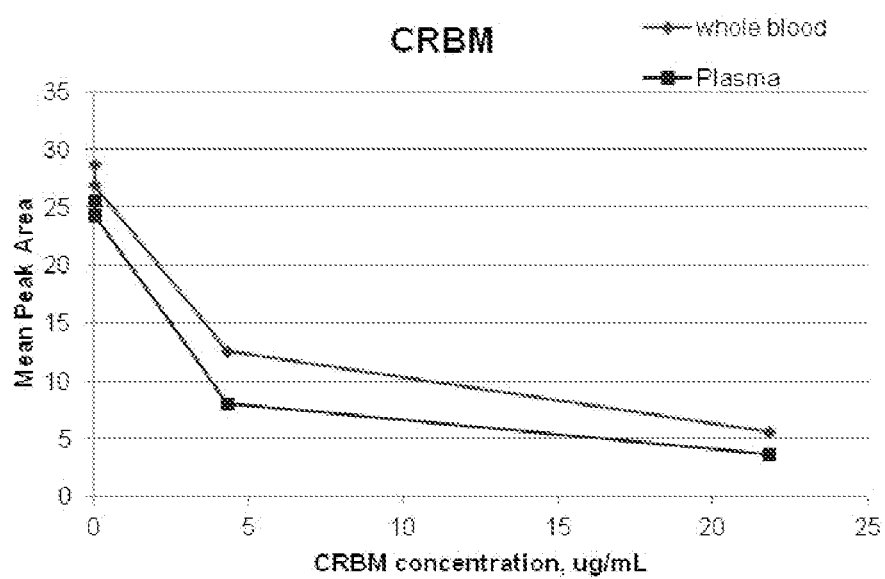
FIG. 6 shows a comparison of dose response curves of carbamazepine using whole blood with interrupting wash protocol to results obtained with plasma.
Figure 7:
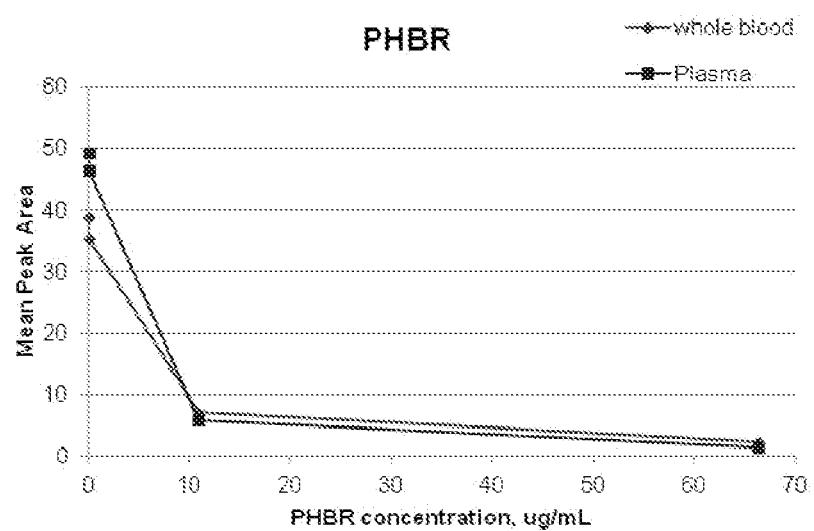
FIG. 7 shows a comparison of dose response curves of phenobarbital using whole blood with interrupting wash protocol to results obtained with plasma.

The resulting dose response curves in FIGS. 6 and 7 demonstrate that whole blood can be directly applied to the micropillar chip in small volumes using the interrupting wash protocol described and yield results which are similar to those obtained with plasma. Both the carbamazepine and phenobarbital competitive assays described were conducted in the presence of whole blood and yielded expected assay results.

Whole blood with filter and interrupting wash: In another embodiment of the invention small volumes of whole blood can be used in a micropillar device by combining filtration and the interrupting wash concepts above. Filters were used to separate red blood cells from plasma from as little as 25 microliters or less of whole blood. The plasma volume transferred to the micropillar structures can be much smaller when used in combination with an interrupting wash protocol. In this embodiment the plasma volume required needs to be sufficient to yield adequate detection signal for the assay but not as large a volume as required to fill the total volume of the chip. Plasma volumes as small as 2 to 6 microliters may be used when combined with a wash.

In this embodiment the whole blood is applied to the filter. The plasma filtrate is transferred to the micropillar space in the sample addition zone and continues to flow through the reagent and detection zones. The flow front is monitored by visual inspection or by the instrument until it reaches a defined distance in the wick zone. The wash fluid is applied to the upstream channel, which prevents or interrupts additional sample from entering the channel, thus controlling the sample volume. The wash fluid flows in both directions which prevents additional plasma from entering the channel and clears the plasma and residual conjugate from the detection (reaction) channel. The wash fluid also serves to fill the remaining chip volume. The fluid front is monitored and read when the wicking zone is completely filled. The interrupting wash can be applied after a consistent sample volume has entered the chip. Ideally this volume should allow for complete dissolution of any reagent material in the reagent zone (such as a conjugate material) but leave sufficient space in the wicking zone for adequate wash.

Whole blood with following wash: In another embodiment, a dose response curve was demonstrated on the fluorescent reader using whole blood with a following wash. The chip used was the reduced volume chip design as shown in FIG. 2, deposited with NT-proBNP reagents (detection antibody aNT-proBNP in the detection/reaction zone and capture antibody aNT-proBNP in the reagent/conjugate zone) with tape covering the wicking zone and detection zone channel. Samples consisted of EDTA whole blood into which a serum sample containing approximately 35000 pg/mL NTproBNP was added following removal of an equal volume of plasma to obtain concentrations of 75, 2220, 4550 and 8942 pg/mL NTproBNP. A solution containing 1% bovine serum albumin, 0.1% Triton X-100, 0.3 mg/mL mouse IgG, 0.3 mg/mL bovine gamma globulin in phosphate buffered saline was used as a pre-wet and wash fluid.

The assay protocol consisted of adding 1 uL wash fluid to the sample addition zone to prewet the flow channel followed by addition of 4 uL whole blood sample to the sample addition zone. The sample is allowed to flow into the micropillar space of the flow channel then 2 uL of wash fluid is added behind the sample addition zone. The wash fluid is allowed to flow entirely into the micropillar space, then the wash step is repeated two more times. The fluid flow is monitored until the wicking zone is completely filled then the chip is read on the reader.

Figure 8:
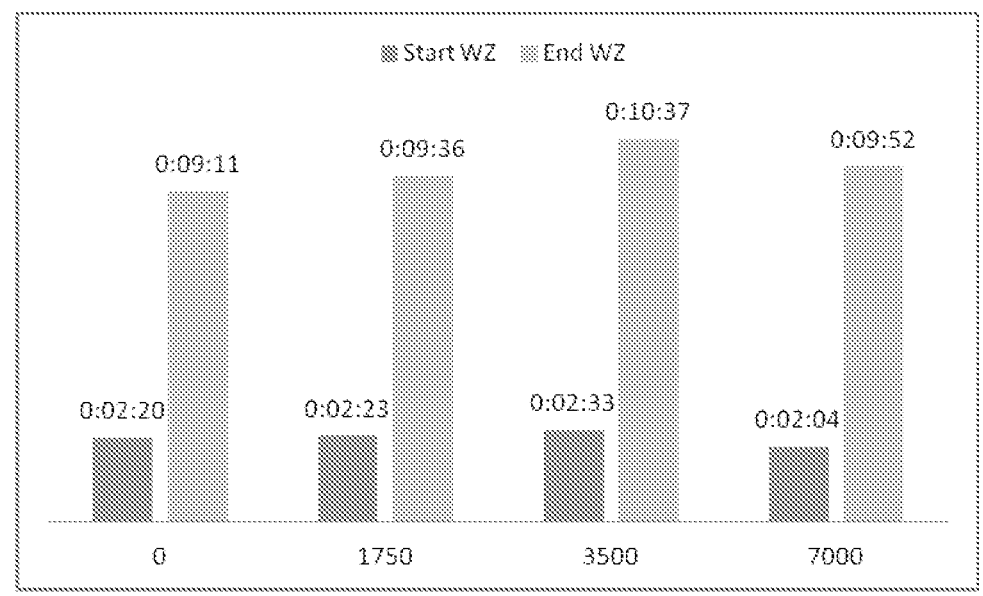
FIG. 8 shows mean flow times for whole blood with a following wash on an assay device according to one embodiment of the present invention, with various NTproBNP levels.
Figure 9:
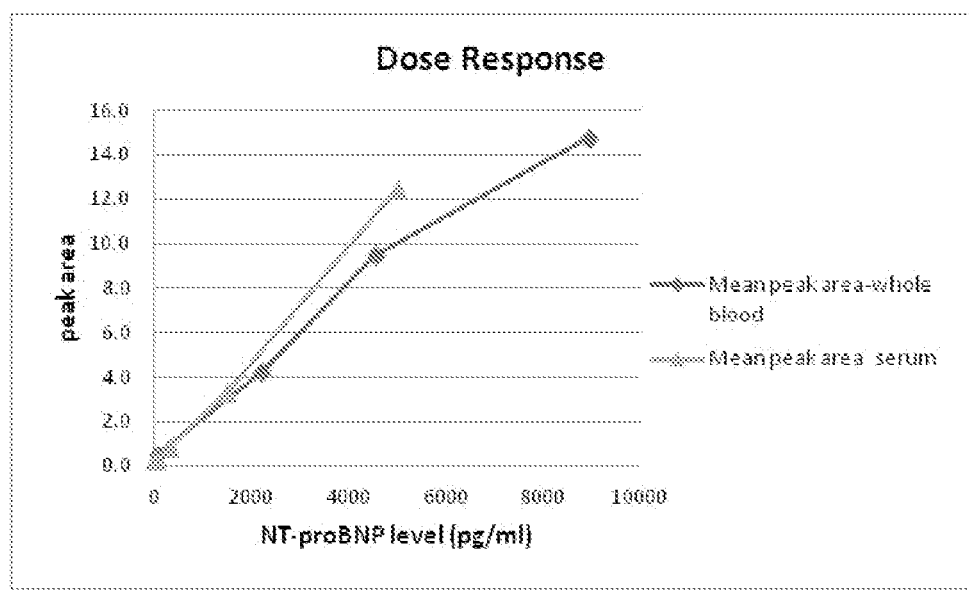
FIG. 9 shows mean peak area of the fluorescent response versus the NTproBNP concentration for each test sample, as well as the dose response curve obtained for whole blood samples compared to serum samples of similar NTproBNP concentration, with a following wash on an assay device according to one embodiment of the present invention.

FIG. 8 shows the mean flow times of three replicates obtained for the whole blood samples with various NT-proBNP levels. These results show that the flow rates throughout the flow channel for these whole blood samples do not vary significantly. FIG. 9 plots the mean peak area of the fluorescent response obtained on the fluorescent reader versus the NT-proBNP concentration for each test sample. FIG. 9 also shows the dose response curve obtained for the whole blood samples compared to serum samples of similar NT-proBNP concentration. These results thus demonstrate that a dose response curve can be obtained with a fluorescent reader by applying whole blood into the flow channel of a reduced volume chip as shown in FIG. 2 and applying a wash fluid before addition of whole blood to facilitate flow and applying an additional wash fluid after addition of whole blood to wash the flow channel.

Example 2

Assay devices made of Zeonor (Zeon, Japan) having oxidized dextran on the surface for covalent immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Serum spiked with NT-proBNP was added to the sample zone of the device and the capillary action of the micropillar array distributed the sample through the flow channel into the wicking zone. Sample volumes of 15 microliters were employed on low-volume device designs R2.02, R2.04, R2.09 and R3.16. The R1.02 device design was a control device, intended for use with 200 microliters of whole blood, such as shown in FIG. 1. R1.02 devices were tested in this example with 45 microliters of serum. A typical assay time was about 10 minutes. The signal intensities from the fluorescently labeled complexes in the detection zone were recorded in a prototype line-illuminating fluorescence scanner.

Figure 10:
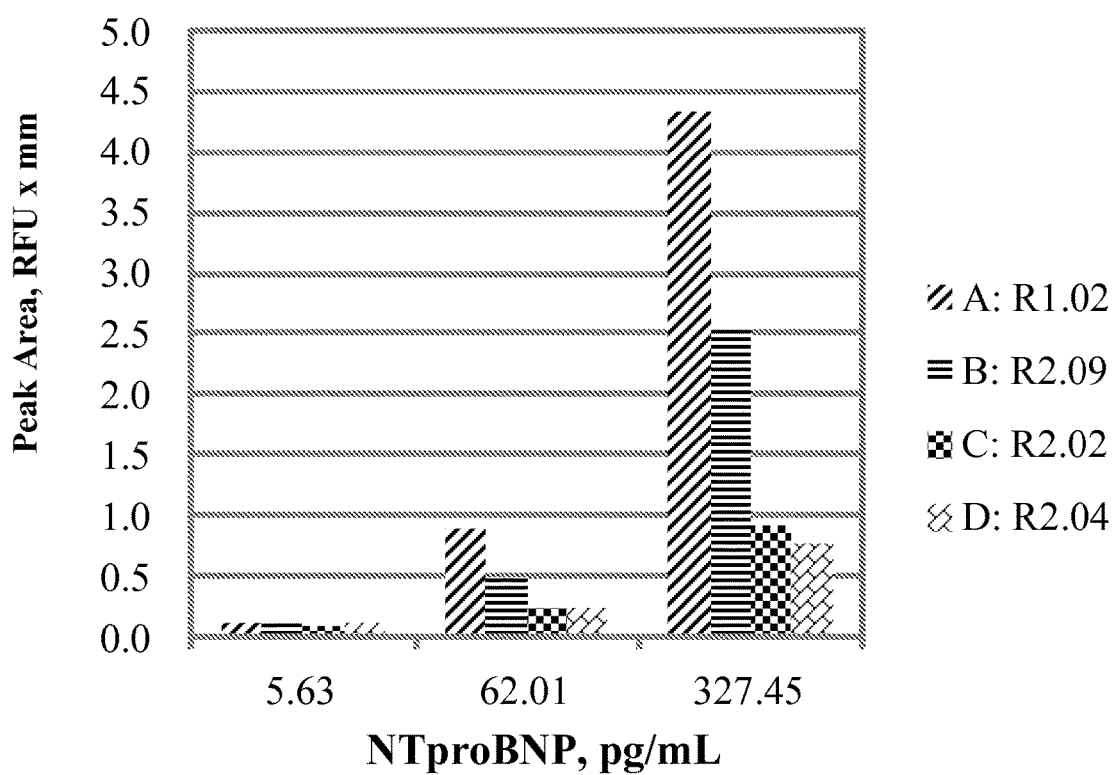
FIGS. 10 and 11 show sensitivity of different assay device designs with NTproBNP as the analyte.
Figure 11:
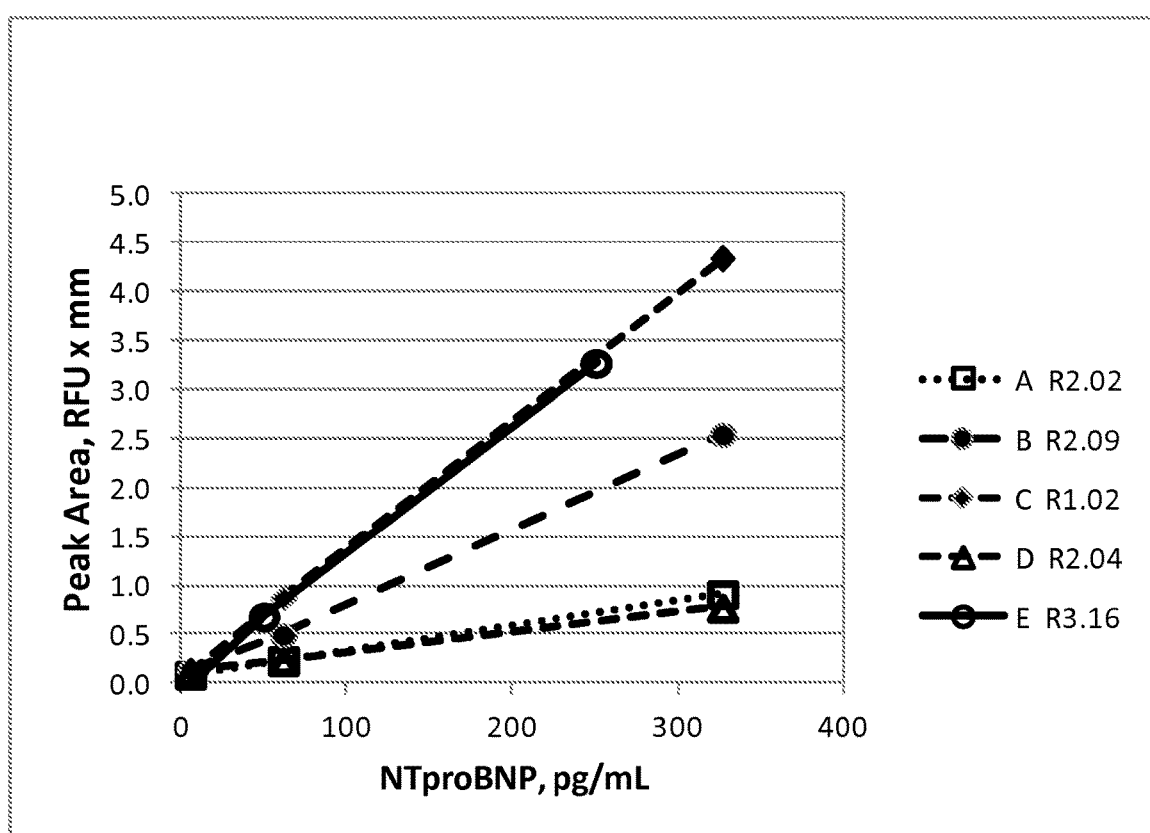

As shown in FIGS. 10 and 11, bar and curve A (R2.02) is a miniaturized device having a single-reagent cell and a directly scaled down detection zone having a detection zone width of 0.5 mm, whereas bar and curve B (R2.09) is a miniaturized device having dual reagent cell and a wider detection zone of 1 mm. Data for two additional device designs is also included for comparison. Bar and curve C (R1.02) is a conventionally sized assay device having a 200 uL whole blood sample volume, and bar and curve D (R2.04) is a single reagent cell device having a 1 mm detection zone width. Curve E (R3.16) includes dual reagent cells and a 1 mm wide detection zone.

Example 3

Figure 12:
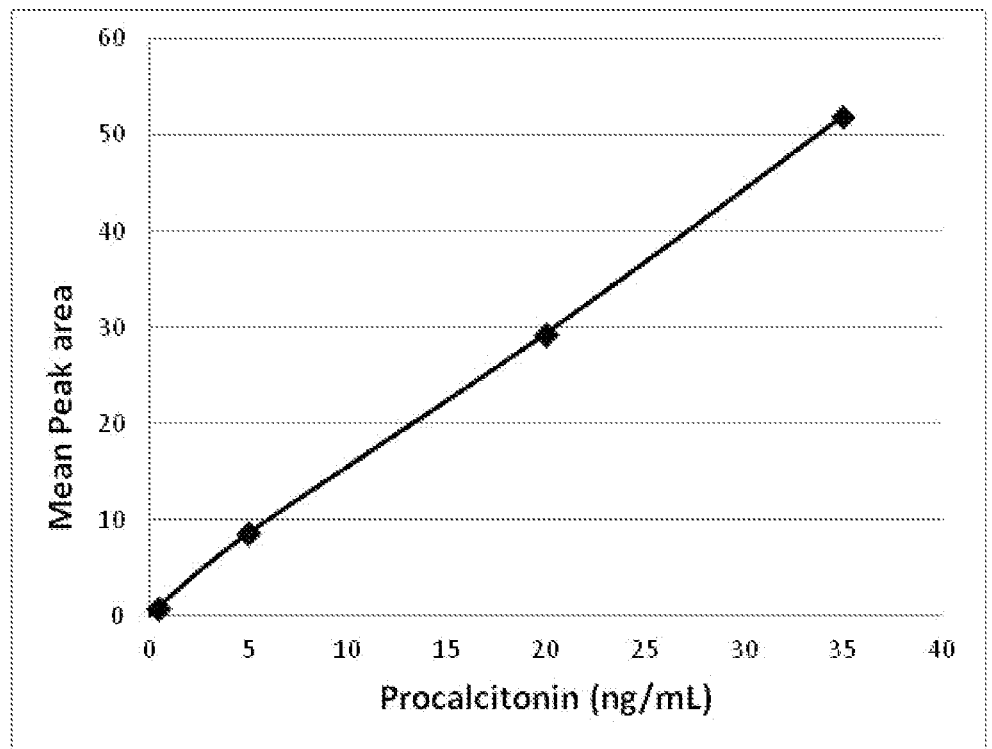
FIG. 12 is a plot of procalcitonin concentration vs. mean peak area using a whole blood sample and a wash.

Miniaturized assay devices having dual reagent cells made of Zeonor (Zeon, Japan) having oxidized dextran on the surface for covalent immobilization of proteins via Schiff base coupling were used. Fluorescently labeled anti-procalcitonin monoclonal antibody was deposited and dried to create a reagent zone. Anti-procalcitonin monoclonal antibody was deposited and dried to create a detection zone. A small amount of Triton X-45 was deposited on the device to increase wettability of the sample for better capillary flow. In this example, 25 microliters of whole blood containing procalcitonin was applied to a filter in contact with the sample addition zone of the assay device. Plasma is transferred from the filter into the sample addition zone and then moves by capillary force through the flow path to the wicking zone. The fluid flow was monitored by visual inspection and 10 microliters of a wash fluid containing 0.01 M phosphate buffer, 0.0027 M potassium chloride, 0.137 M sodium chloride, 1% bovine serum albumin and 0.1% triton X-100 was added to the reagent addition zone when the fluid flow front filled 20% of the wicking zone. The assay device was inserted into a fluorescent reader immediately after the wicking zone was determined to be completely filled. The fluorescent signal within the detection zone was measured and the peak area under the response curve was determined for each sample. Whole blood samples were collected fresh from normal donors in lithium heparin tubes. A concentrated serum sample containing 10 µg/mL procalcitonin was added to aliquots of whole blood to create samples containing 0, 0.4, 5, 20 and 35 ng/mL procalcitonin. FIG. 12 plots the mean peak area of five replicate results for each sample versus the procalcitonin concentration. As FIG. 12 demonstrates, using a small sample size (i.e., 25 μL whole blood/10 μL wash) provides satisfactory results over a wide range of analyte concentrations.

Example 4

Figure 13:
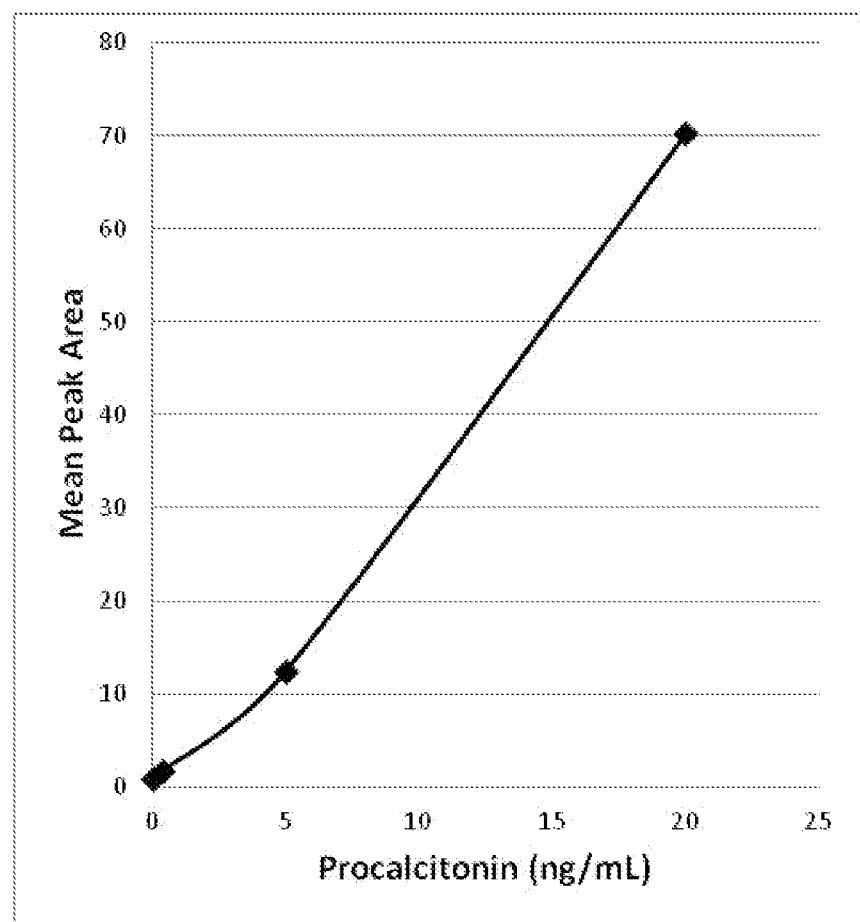
FIG. 13 is a plot of procaloitonin concentration vs. mean peak area using a whole blood sample.

Miniaturized assay devices having dual reagent cells made of Zeonor (Zeon, Japan) having oxidized dextran on the surface for covalent immobilization of proteins via Schiff base coupling were used. Fluorescently labeled anti-procalcitonin monoclonal antibody was deposited and dried to create a reagent zone. Anti-procalcitonin monoclonal antibody was deposited and dried to create a detection zone. A small amount of Triton X-45 was deposited on the device to increase wettability of the sample for better capillary flow. In this example, 35 μl of whole blood containing procalcitonin was applied to a filter in contact with the sample addition zone of the assay device. Plasma is transferred from the filter into the sample addition zone then moves by capillary force through the fluid flow path to the wicking zone. The fluid flow was monitored by visual inspection and inserted into the fluorescent reader immediately after the wicking zone was determined to be completely filled. The fluorescent signal within the detection zone was measured and the peak area under the response curve was determined for each sample. Whole blood samples were collected fresh from normal donors in EDTA tubes. A concentrated serum sample of 10 μg/mL procalcitonin was added to aliquots of whole blood to create samples containing 0, 0.4, 5, and 20 ng/mL procalcitonin. FIG. 13 plots the mean peak area of three replicate results for each sample versus the procalcitonin concentration. As FIG. 13 demonstrates, using a small sample size (i.e., 35 μL whole blood) provides satisfactory results over a wide range of analyte concentrations.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

Copending applications entitled "Low Volume Assay Device Having Increased Sensitivity" (U.S. Provisional Appl. No. 61/588,758, first named inventor: Phil Hosimer), "Assay Device Having Multiple Reagent Cells" (U.S. Provisional Appl. No. 61/588,738, first named inventor: Zhong Ding), "Assay Device Having Uniform Row Around Corners" (U.S. Provisional Appl. No. 61/588,745, first named inventor: James Kanaley), "Controlling Fluid Flow Through An Assay Device" (U.S. Provisional Appl. No. 61/588,772, first named inventor James Kanaley), and "Assay Device Having Multiplexing" (U.S. Provisional Appl. No. 61/588,779, first named inventor: Sue Danielson), all filed concurrently herewith are all incorporated herein by reference in their entireties.

We claim:

1. An assay device comprising:
a liquid sample addition zone;
a reagent zone downstream and in fluid communication with the liquid sample addition zone, the reagent zone containing a reagent material;
a detection zone in fluid communication with the reagent zone having capture elements bound thereto; and
a wicking zone in fluid communication with the detection zone having a capacity to receive a liquid sample flowing from the detection zone,
wherein the liquid sample addition zone, the reagent zone, the detection zone, and the wicking zone define a fluid flow path,
further comprising a reagent addition zone along and in fluid communication with the fluid flow path downstream from the liquid sample addition zone and upstream of the detection zone, the reagent addition zone having a width that is greater than a width of the fluid flow path and less than a width of the liquid sample addition zone to receive a reagent fluid from a reagent source,
wherein the liquid sample addition zone is configured to receive a sample and enable the sample to move through the fluid flow path, and
wherein the width of the reagent addition zone is configured to enable enough volume of the received reagent fluid to be added to the fluid flow path to interrupt flow of the sample through the fluid flow path and control a sample size of the sample within the fluid flow path.

2. An assay device as claimed in claim 1, wherein at least a part of the fluid flow path has a substrate surface and projections that extend substantially vertically from the substrate surface, and wherein the projections have a height, a cross section, and a distance between one another that defines a space between the projections capable of generating capillary flow parallel to the substrate surface.

3. An assay device as claimed in claim 1, wherein the reagent addition zone is downstream from the reagent zone.

4. An assay device as claimed in claim 1, wherein the reagent addition zone comprises a reservoir.

5. An assay device as claimed in claim 1, wherein the reagent material comprises a labeled reagent material.

6. An assay device as claimed in claim 1, wherein the liquid sample addition zone comprises a surfactant deposited thereon.

7. An assay device as claimed in claim 1, further comprising a filter located on the liquid sample addition zone, wherein the sample passes through the filter before entering the fluid flow path.

8. An assay device as claimed in claim 1, further comprising a hydrophilic tape at least partially covering the detection zone.

9. A method of performing an assay on a liquid sample for the detection of one more analytes of interest, the method comprising:
providing a liquid sample addition zone;
providing a reagent zone downstream from and in fluid communication with the liquid sample addition zone, the reagent zone containing a reagent material;
providing a detection zone in fluid communication with the reagent zone;
providing a wicking zone in fluid communication with the detection zone having a capacity to receive a liquid sample flowing from the detection zone, wherein the liquid sample addition zone, the reagent zone, the detection zone, and the wicking zone define a fluid flow path;
further providing a reagent addition zone along and in fluid communication with the fluid flow path downstream from the liquid sample addition zone and upstream of the detection zone, the reagent addition zone having a width that is greater than a width of the fluid flow path and less than a width of the liquid sample addition zone to receive a reagent from a reagent source;

adding the liquid sample containing the analyte of interest onto the liquid sample addition zone;

adding the reagent to the reagent addition zone, thereby interrupting flow of the liquid sample through the fluid flow path for controlling a sample size of the liquid sample within the fluid flow path;

moving the liquid sample by capillary action into the reagent zone, wherein the liquid sample dissolves the reagent material;

flowing the liquid sample away from the reagent zone with the dissolved reagent material therein into the detection zone by capillary action, wherein the analyte of interest is detected in the detection zone by reading a signal that is generated; and flowing the liquid sample and any unbound material into the wicking zone.

10. A method as claimed in claim 9, wherein the reagent is added to the reagent addition zone when the liquid sample has moved into the wicking zone.

11. A method as claimed in claim 9, wherein the reagent is added to the reagent addition zone when the liquid sample has moved into 50% of the wicking zone.

12. A method as claimed in claim 9, wherein the reagent added to the reagent addition zone is a wash reagent.

13. A method as claimed in claim 9, wherein the liquid sample moves from the detection zone and into the wicking zone, and the signal is read immediately or a short time after the liquid sample has moved through the detection zone.

14. A method as claimed in claim 9, wherein one or more washes follow the liquid sample through the fluid flow path to wash any unbound detection element away from the detection zone.

15. A method as claimed in claim 9, wherein the reagent material is labeled with a detection element.

16. A method as claimed in claim 15, wherein the detection zone contains capture elements to capture the detection element.

17. A method as claimed in claim 16, wherein the signal is generated by the detection element.

* * * * *